(12) United States Patent
Singh et al.

(10) Patent No.: US 8,765,807 B2
(45) Date of Patent: *Jul. 1, 2014

(54) ESTERS OF CAPSAICIN FOR TREATING PAIN

(75) Inventors: Chandra Ulagaraj Singh, San Antonio, TX (US); Jagaveerabhadra Rao Nulu, Austin, TX (US)

(73) Assignee: Trinity Laboratories, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/108,419

(22) Filed: May 16, 2011

(65) Prior Publication Data

US 2011/0218180 A1 Sep. 8, 2011

Related U.S. Application Data

(63) Continuation of application No. 11/878,335, filed on Jul. 24, 2007, now Pat. No. 7,943,666.

(60) Provisional application No. 60/832,599, filed on Jul. 24, 2006.

(51) Int. Cl.
*A01N 37/00* (2006.01)
*A61K 31/21* (2006.01)
*A01N 37/18* (2006.01)
*A61K 31/16* (2006.01)

(52) U.S. Cl.
USPC .......................................... 514/506; 514/625

(58) Field of Classification Search
None
See application file for complete search history.

(56) References Cited

U.S. PATENT DOCUMENTS

| 3,903,297 | A | * | 9/1975 | Robert | 514/530 |
| 4,113,881 | A | * | 9/1978 | Diehl | 514/549 |
| 4,599,342 | A | * | 7/1986 | LaHann | 514/282 |
| 2006/0240097 | A1 | * | 10/2006 | Jamieson et al. | 424/451 |

FOREIGN PATENT DOCUMENTS

EP 0149545 A2 * 7/1985

OTHER PUBLICATIONS

Fang et al. International Journal of Pharmaceutics 131 (1996) 143-151.*

* cited by examiner

*Primary Examiner* — Layla Bland
(74) *Attorney, Agent, or Firm* — Nevrivy Patent Law Group P.L.L.C.

(57) ABSTRACT

The present invention relates to the formulations of ester derivatives of capsaicin and ester derivatives of myristoleic acid. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The pharmaceutical compositions are useful for pain management in mammals in vivo and have been contemplated to be used in the treatment of various pains in humans.

22 Claims, 3 Drawing Sheets

FIGURE 1. The Chemical Structures of Capsaicins.

FIGURE 2. Formula Ia: The Chemical Structures of Capsaicin Esters

1. Capsaicin Ester           $R1 = (CH_2)_4(CH)_2CH(CH_3)_2$

2. Homocapsaicin Ester       $R1 = (CH_2)_4(CH)_2CH(CH_3)_2$

3. Nordihydrocapsaicin Ester   $R1 = (CH_2)_5(CH)_2CH(CH_3)_2$
4. Dihydrocapsaicin Ester      $R1 = (CH_2)_6CH(CH_3)_2$
5. Homodihydrocapsaicin Ester  $R1 = (CH_2)_7CH(CH_3)_2$ 6. n-Vanillyloctanamide Ester  $R1 = (CH_2)_6CH_3$
7. Nonivamide Ester            $R1 = (CH_2)_7CH_3$
8. n-Vanillyldecanamide Ester  $R1 = (CH_2)_8CH_3$

FIGURE 3. Formula Ib: The Chemical Structures of Myristoleic Acid Esters

Cetyl Myristoleate  R = -$(CH_2)_{15}$-$CH_3$

ESTERS OF CAPSAICIN FOR TREATING PAIN

CROSS-REFERENCE TO RELATED APPLICATIONS

This application is a continuation of U.S. patent application Ser. No. 11/878,335, filed Jul. 24, 2007, which claims the benefit of Provisional Patent Application Ser. No. 60/832,599, filed Jul. 24, 2006.

FEDERALLY SPONSORED RESEARCH

None

SEQUENCE LISTING OR PROGRAM

None

FIELD OF INVENTION

This invention relates to a treatment for pain. More specifically it relates to the use of esters of capsaicin for the treatment of pain. Even more specifically it relates to the use of esters of capsaicin and ester derivatives of myristoleic acid for the treatment of pain.

BACKGROUND OF THE INVENTION

*Capsicum* consists of the dried ripe fruits of *Capsicum annuum* Roxb. (Family Solanaceae), a small erect shrub indigenous to tropical America, cultivated in South America, China, India and Africa. *Capsicum* contains a crystalline pungent principle capsaicin, traces of a liquid alkaloid, red coloring matter and a fatty oil. In folk medicine, *capsicum* is regarded as an aphrodisiac, depurative, digestive, stomachic, carminative, antispasmodic, diaphoretic, antiseptic, counter-irritant, rubefacient, stypic, and tonic. Internally, *capsicum* has been used to treat asthma, pneumonia, diarrhea, cramps, colic, toothache, flatulent dyspepsia without inflammation; insufficiency of peripheral circulation; as a gargle for sore throat, chronic pharyngitis and laryngitis; and externally as a lotion or ointment to treat neuralgia, including rheumatic and arthritic pain, and unbroken chilblains (cold injuries) (Duke, 1985; Leung and Foster, 1996; Newall et al., 1996).

In Germany, cayenne pepper is official in the *German Pharmacopeia* and approved in the Commission E monographs as a topical ointment for the relief of painful muscle spasms in the upper torso (DAB, 1997). In the United States, *capsicum* tincture and oleoresin were formerly official in the *United States Pharmacopeia* and *National Formulary*. *Capsicum* USP was used as a carminative, stimulant, and rubefacient (Leung and Foster, 1996; Taber, 1962).

Figure 1:
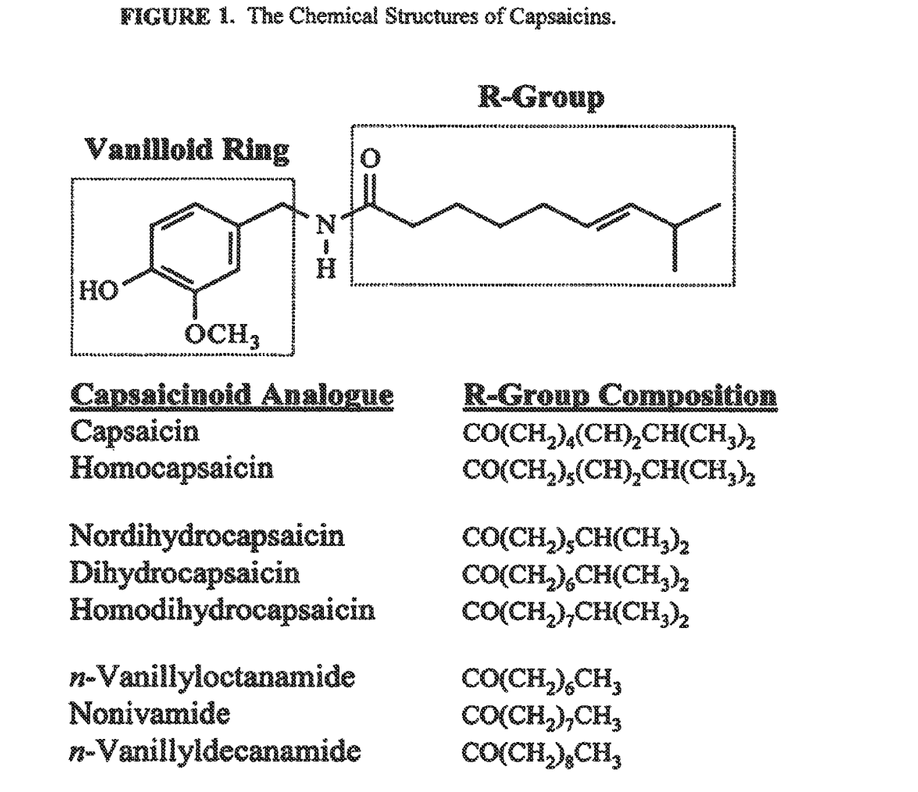
FIG. 1. is a picture of the chemical structures of capsaicins.
Figure 2:
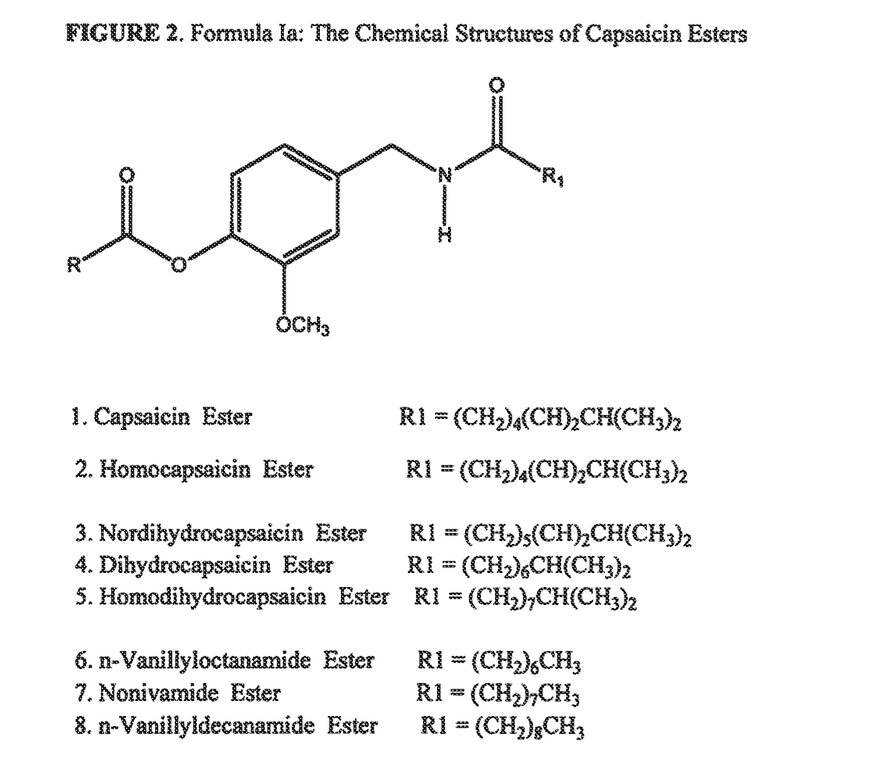
FIG. 2. is a picture of the formula of the chemical structures of capsaicin esters.

The most potent and predominant chemical entity in *capsicum* is capsaicin (0.14%) (Cordell and Araujo, 1993; FIG. 1). The heat sensation of pure capsaicin is approximately 16 million Scoville heat units (SHU) and is so hot that in its pure form diluted one hundred thousand fold it can cause blistering of the tongue. A series of homologous branched- and straight-chain alkyl vanillylamides, collectively known as capsaicinoids, is present in lesser concentrations than the parent compound, capsaicin. Of the capsaicinoid fraction, capsaicin (48.6%) is quantitatively followed by 6,7-dihydrocapsaicin (36%), nordihydrocapsaicin (7.4%), homodihydrocapsaicin (2%), and homocapsaicin (2%) (Duke, 1985). Capsaicinoids and capsaicin are collectively found in amounts of 0.1% to 1%, with quantities varying according to soil and climate (Rumsfield and West, 1991).

Capsaicin, a colorless crystalline substance, was first synthesized in 1930. Capsaicin has been studied since the mid-19th century and its structure is elucidated as 8-methyl-6-nonenoyl vanillylamide (Cordell and Araujo, 1993). Most pharmacological studies performed with isolated constituents of chile pepper have focused on capsaicin, which is the major pungent constituent.

The crude extract of *capsicum* fruits, known as *capsicum* oleoresin, contains at least 100 different volatile chemical constituents, and therefore may function in differing ways from pure capsaicin. Thus, it is important to distinguish between studies using capsaicin and those employing *capsicum* oleoresin (Cordell and Araujo, 1993).

Nonivamide (pelargonic acid vanillylamide) is a common synthetic adulterant of *capsicum* products. Although structurally different from capsaicin, its presence in *capsicum* or capsaicin samples can be detected spectrographically and there is no evidence that this compound occurs naturally in *Capsicum* (Cordell and Araujo, 1993).

Capsaicin affects lipid metabolism as demonstrated in a study by Kawada et al. (1986). Male rats fed a diet containing 30% lard with capsaicin at 0.14% of the diet developed serum triglyceride levels that were significantly lower than those of animals receiving a high-fat diet without capsaicin. But levels of free fatty acids, cholesterol, and pre-beta-lipoprotein were not affected. Activities of liver enzymes involved in lipid synthesis (acetyl-CoA carboxylase) and in carbohydrate metabolism (glucose-6-phosphate dehydrogenase) were inhibited in the high-fat diet, but the activity of the latter was restored to control levels by the added dietary capsaicin. The weight of perirenal adipose tissue was reduced in a dose-dependent manner by capsaicin. These results suggested that capsaicin did not interfere with lipid biosynthesis. Rather, that capsaicin might stimulate lipid metabolism, and possibly facilitates mobilization of lipid from adipose tissue.

In a follow-up to the study above, Kawada et al. (1986a) measured the effect of i.p. administered capsaicin on general energy metabolism, including oxygen consumption, respiratory quotient, and substrate utilization. Capsaicin had a general stimulatory effect on metabolism, similar to that of epinephrine; oxygen consumption was elevated, respiratory quotient was initially elevated, then decreased; and serum glucose and insulin levels were elevated, concomitant with a rapid decrease in liver glycogen, and a gradual increase in serum triglycerides. The response was blocked by beta-adrenergic blockers, but was not effected by alpha-adrenergic or ganglion blockers. Their results suggested that capsaicin effects metabolism either as a direct beta-adrenergic agonist, or indirectly by stimulating catecholamine release.

Yamato et al. (1996) showed that capsaicin produced a marked concentration-dependent decrease in the amplitude, the rate of rise, and the rate of relaxation of the contractile tension of rat ventricular papillary muscles; however, the half-life of the relaxation and the time to peak tension were only slightly effected. Calcium release and shortening of action potential duration in ventricular myocytes was profoundly reduced by capsaicin, perhaps resulting from the non-specific membrane-stabilizing effects of capsaicin.

Capsaicin treatment caused a biphasic effect on contractile force, left ventricular systolic blood pressure, and heart rate of isolated perfused rat hearts. A transient initial increase in contractile force and left ventricular systolic pressure was observed, followed by a prolonged depression of both parameters. Heart rate was increased, but this effect was not followed by a subsequent reduction. The initial increases in contractile force and blood pressure could have been induced by the release of calcitonin-gene-related peptide (CGRP) from local sensory nerves; the negative inotropic effects following the initial increase may be due to a direct inhibitory effect of capsaicin on ventricular cells, or to nonspecific membrane-stabilizing effects. The increased heart rate was attributed to the release of CGRP (Lundberg 1985).

Capsaicin elicits a vasoconstrictive response in the large cerebral arteries of the cat (Saito et al., 1988), and in the middle and basilar cerebral arteries, an effect was attributed to a direct contraction of smooth muscle, since the response was independent of the presence of endothelium and nerve components. However, Saito et al. found results suggesting that while capsaicin releases and depletes vasodilator peptides from perivascular nerves, the direct vasoconstrictor effects of capsaicin overwhelm the vasodilator effects of these peptides.

An increased activity of CGRP-containing trigeminovascular nerve fibres has been correlated to the pathophysiology of migraine (Buzzi et al., 1991) either during attacks (Goadsby et al., 1990; Goadsby & Edvinsson, 1993) or as ageneral imbalance in migraine patients (Ashina et al., 2000). Therefore, clinical potentials of CGRP receptor antagonists in the treatment of migraine have been addressed (Doods et al., 2000). Capsaicin (Holzer, 1991b; Szallasi & Blumberg, 1999) potently and selectively causes release of CORP from sensory nerve terminals both in vitro and in vivo (Duckles & Levitt, 1984; Duckles, 1986; Holzer, 1991a; Saito & Goto, 1986; Wharton et al., 1986). The mechanism of capsaicin-induced CGRP depletion involves binding of capsaicin to vanilloid 1 receptors (VR1) (Caterina et al., 1997). Capsaicin-association to VRs triggers Ca2+ influx and elevated intracellular calcium levels in turn stimulate CGRP-release. The vanilloid 1 receptor is in addition to capsaicin stimulated by heat, hydrogen ions, lactate (Franco-Cereceda & Liska, 2000; Franco-Cereceda, 1988) and the endogeneous cannabinoid, anandamide (Zygmunt et al., 1999).

A hypoxic reflectory release of CGRP which has been suggested in myocardium (Kallner, 1998; Dai et al., 2000; Franco-Cereceda & Liska, 2000) and in cerebral arteries (Mc-Culloch et al., 1986) may be due to stimulation of this receptor as well. It has previously been demonstrated that CGRP, rather than SP and NKA, is responsible for the capsaicin-induced vasodilatation of guinea-pig basilar artery (Franco-Cereceda & Rudehill, 1989; O'Shaughnessy et al., 1993; Jansen-Olesen et al., 1996).

In tests using cultured human intestinal epithelial cells, Jensen-Jarolim et al. (1998) found sufficient in vitro evidence to suggest that *Capsicum* may increase the permeability of the gastrointestinal tract to allow transport of macromolecules and ions across the epithelium; an effect, they add, that might have importance to food intolerance and allergic reactions to food. The stimulatory effect of orally administered capsaicin on gastric acid secretion and mucosal blood flow was studied in rats using amounts roughly equivalent to a normal Thai diet. Capsaicin was noted to have a protective effect on gastric mucosa of ethanol-induced gastric lesions in rats (Uchida et al., 1991). The protective effect was attenuated upon pretreatment with indomethacin and disappeared in capsaicin-sensitive nerve-degenerated rats, suggesting that enhanced prostaglandin formation inhibited lesion formation. Further study by the same group found decreased stomach motility and increased mucosal blood flow with intragastric capsaicin treatment, whereas capsaicin pre-treatment desensitized the afferent neurons, thereby mitigating this protective effect.

An in vitro chemopreventive activity of capsaicin was shown by Morr et al. (1995). When capsaicin was added to cultured cells of Caov-3 human ovarian carcinoma, MCF-10A human mammary adenocarcinoma, HL-60 human pro-myelocytic leukemia, and HeLa cells, a preferential growth-inhibition was evident as cells became smaller and underwent cell death. Condensed and appearing fragmented, the nuclear DNA of these cells suggested that capsaicin had induced apoptosis.

The arachidonic acid cascade is an important component of inflammation and the associated localized immune response. The release of arachidonic acid (AA) from membrane phospholipids and subsequent leukotriene biosynthesis occurs during inflammation, and products formed by AA oxidation act in concert with numerous other factors, including cytokines, PAF (platelet-activating factor), nitrogen oxide, and histamine, all of which are important mediators of the immune response. A study (Panossian et al., 1996) found that at low concentrations capsaicin stimulated the production of interleukin-1a, while at higher doses it inhibited this response. Capsaicin caused a dose-dependent release of AA from PMNs (poly-morphonuclear leukocytes), and a similar concentration-dependent conversion of the AA metabolites, prostaglandin E2 (PGE2) and LTB4. When incubated with granulocytes, capsaicin caused an increased synthesis of 12-HETE, an eicosanoid metabolite of AA, but at the same time was found to cause a dose-dependent decrease of all products of 5-lipoxygenase. These results suggested that the dose-dependent reversible effects of capsaicin on immune cells and interleukin-1alpha are closely associated with arachidonic acid metabolism (Panossian et al., 1996).

Viral replication, immune regulation, and induction of various inflammatory and growth-regulatory genes require activation of a nuclear transcription factor (NF)-κ-B. Agents that can block NF-κ-B activation have potential to block downstream responses mediated through this transcription factor. Capsaicin (8-methyl-N-vanillyl-6-nonenamide) has been shown to regulate a wide variety of activities that require NF-κ-B activation (Singh 1996). The pretreatment of human myeloid ML-1a cells with capsaicin blocked TNF-mediated activation of NF-κ-B in a dose- and time-dependent manner. Capsaicin treatment of cells also blocked the degradation of I-κ-B alpha, and thus the nuclear translocation of the p65 subunit of NF-κ-B, which is essential for NF-κ-B activation. TNF-dependent promoter activity of I-κ-B alpha, which contains NF-κ-B binding sites, was also inhibited by capsaicin.

Neurogenic inflammation has been successfully modeled using capsaicin. When injected intradermally, capsaicin evokes a temporary burning sensation lasting 3 to 5 minutes and a characteristic localized flare consisting of a red flush with slight edema (Holzer 1988). The capsaicin flare is thought to be induced by a local axon reflex involving release of neuropeptides such as SP and CGRP from sensory neurons (Holzer 1988). Additional mediators of the capsaicin flare are thought to include cytokines, prostaglandins, and other neuropeptides (Holzer 1991; Veronesi 1999). Within normal individuals, the size of the capsaicin flare over time is quite consistent (Jolliffe 1995).

The effect of glucocorticoids and catecholamines on the capsaicin-induced flare have been minimally examined. However, glucocorticoids have not been shown to block the capsaicin-induced flare (Ahluwalia 1994). Alpha adrenoreceptors are known to be involved in the pain response to capsaicin (Kinnman 1997).

Depending on the concentration used and the mode of application, capsaicin can selectively activate, desensitize, or exert a neurotoxic effect on small diameter sensory afferent nerves while leaving larger diameter afferents unaffected (Holzer, 1991; Winter et al., 1995). Sensory neuron activation occurs due to interaction with a ligand-gated nonselective cation channel termed the vanilloid receptor (VR-1) (Caterina et al., 1997), and receptor occupancy triggers $Na^+$ and $Ca^{2+}$ ion influx, action potential firing, and the consequent burning sensation associated with spicy food or capsaicin-induced pain. VR1 receptors are present on both C and Aδ fibers, and can be activated by capsaicin and its analogs, heat, acidification, and lipid metabolites (Tominaga et al., 1998; Caterina and Julius, 2001). Desensitization occurs with repeated administration of capsaicin, is a receptor-mediated process, and involves $Ca^{2+}$- and calmodulin-dependent processes and phosphorylation of the cation channel (Winter et al., 1995; Wood and Docherty, 1997).

Capsaicin induces release of substance P and calcitonin gene-related peptide from both peripheral and central terminals of sensory neurons, and desensitization inhibits such release (Holzer, 1991); such inhibition may result from inhibition of voltage-gated $Ca^{2+}$-currents (Docherty et al., 1991; Winter et al., 1995). Neurotoxicity is partially osmotic and partially due to $Ca^{2+}$ entry with activation of $Ca^{2+}$-sensitive proteases (Wood et al., 1989; Winter et al., 1995). In neonates, neurotoxicity can be lifelong (Jansco et al., 1977), whereas in adult animals receiving a localized dose, a reversible injury may occur as cell bodies capable of regeneration are left intact (Holzer, 1991). Both desensitization and neurotoxicity lead to analgesia in rodent paradigms, with specific characteristics of analgesia depending on the dose of capsaicin, route of administration, treatment paradigm (i.e., acute or repeated administration), and age of the animal (Holzer, 1991; Winter et al., 1995). The topical skin application of capsaicin to rodents produces analgesia (Kenins, 1982; Lynn et al., 1992), but variability in outcome can occur due to the concentration, the number of applications, and the different vehicles used that can affect the rate and extent of skin penetration (Carter and Francis, 1991; McMahon et al., 1991).

The distribution and metabolism of capsaicin and/or dihydrocapsaicin has been studied in rats. Capsaicin is distributed to the brain, spinal cord, liver and blood within 20 mins. of i.v. administration. Oral doses of dihydrocapsaicin in the rat showed metabolic activity associated with its absorption into the portal vein. Capsaicin and dihydrocapsaicin are metabolized in the liver by the mixed-function oxidation system (cytochrome P-450-dependent system). It is assumed that capsaicin is excreted in urine. In rats, most of dihydrocapsaicin is known to be rapidly metabolized and excreted in the urine (Rumsfield and West, 1991).

Acute intradermal injection of capsaicin to the skin in humans produces a burning sensation and flare response; the area of application becomes insensitive to mechanical and thermal stimulation, the area of flare exhibits a primary hyperalgesia to mechanical and thermal stimuli, and an area beyond the flare exhibits secondary allodynia (Simone et al., 1989; LaMotte et al., 1991). Repeated application to normal skin produces desensitization to this response and thus forms the basis of the therapeutic use of topical capsaicin in humans. Desensitization involves both physiological changes in the terminals of the sensory neuron noted above, as well as a degree of loss of sensory fiber terminals within the epidermis (Simone et al., 1989; Nolano et al., 1999). With respect to topical applications of capsaicin, it has been estimated that assuming 100% of a topically-applied dose is absorbed into the body, an application of 90 g capsaicin (2 tubes of cream, 0.025% capsaicin) per week would result in a daily exposure of 0.064 mg/kg capsaicin for a 50 kg person. This represents less than 10% of the dietary intake of a typical Indian or Thai diet (Rumsfield and West, 1991).

Topical capsaicin preparations of 0.025 and 0.075% are available for human use, and these produce analgesia in randomized double-blind placebo-controlled studies, open label trials, and clinical reports (Watson, 1994; Rains and Bryson, 1995). Capsaicin, is recognized by the U.S. FDA as a counterirritant for use in OTC topical analgesic drug products (Palevitch and Craker, 1995). It is used as a component in various counterirritant preparations (Leung and Foster, 1996), including ArthriCare® (Del Pharmaceuticals, Inc.) arthritis pain relieving rub, which contains *Capsicum* oleoresin (0.025% capsaicin) in combination with menthol USP and *Aloe vera* gel (Arky et al., 1999). *Capsicum* ointments, such as Zostrix® cream (GenDerm Corp.), containing 0.025% or 0.075% capsaicin, are used topically to treat shingles (herpes zoster) and post-herpetic neuralgia (Bernstein et al., 1987; Der Marderosian, 1999; Palevitch and Craker, 1995).

Topical capsaicin produces benefit in post-herpetic neuralgia (Bernstein et al., 1989; Watson et al., 1993), diabetic neuropathy (Capsaicin Study Group, 1992), postmastectomy pain syndrome (Watson and Evans, 1992; Dini et al., 1993), oral neuropathic pain, trigeminal neuralgia, and temperomandibular joint disorders (Epstein and Marcoe, 1994; Hersh et al., 1994), cluster headache (following intranasal application; Marks et al., 1993), osteoarthritis (McCarthy and McCarthy, 1992), and dermatological and cutaneous conditions (Hautkappe et al., 1998). Whereas pain relief is widely observed in these studies, the degree of relief is usually modest, although some patients have a very good result. Topical capsaicin is generally not considered a satisfactory sole therapy for chronic pain conditions and is often considered an adjuvant to other approaches (Watson, 1994). No significant benefit was reported in chronic distal painful neuropathy (Low et al., 1995) or with human immunodeficiency virus-neuropathy (Paice et al., 2000).

Capsaicin produces marked alterations in the function of a defined subpopulation of unmyelinated sensory afferents, termed C-polimodal nociceptors. Following the initial period of intense burning or stinging pain accompanied by erythema, topical capsaicin application causes insensitivity to further irritation by a variety of noxious stimuli. Accordingly, topical preparations of capsaicin find use as a topical therapy for a variety of cutaneous disorders that involve pain and itching, such as post-herpetic neuralgia, diabetic neuropathy, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis (Hautkappe et al., 1998).

The most frequently encountered adverse effect with capsaicin is burning pain at the site of application, particularly in the first week of application. This can make it impossible to blind trials and can lead to dropout rates ranging from 33 to 67% (Watson et al., 1993; Paice et al., 2000). Another factor in compliance is the time delay before therapeutic effect is observed (at least a week, but sometimes several weeks). One approach toward minimizing adverse effects and accelerating the rate of analgesia has been to deliver a higher capsaicin concentration (5-10%) under regional anesthesia, and this produced sustained analgesia lasting 1 to 8 weeks in cases of complex regional pain syndrome and neuropathic pain (Robbins et al., 1998). When topical local anesthetics were applied with 1% topical capsaicin, no alteration in pain produced by the capsaicin was observed in healthy subjects (Fuchs et al., 1999) indicating that this co-treatment was not sufficient to block the pain induced by capsaicin.

Because of intense burning or stinging pain, many patients are not tolerated in the long-term treatment with topical capsaicin and, therefore, have to discontinue the treatment before appearance of analgesic effect of capsaicin through prolonged administration. It was reported that 26 out of 39 (66.7%) patients suffering from post-herpetic neuralgia were not tolerated with a 0.025% capsaicin preparation (Zostrix, Gen Derm, USA). With a 0.075% preparation (Zostrix-HP, Gen Derm, USA), 5 out of 16 (31.3%) and 45 out of 74 (60.8%) patients with post-herpetic neuralgia were not tolerated (Peikert et al., 1991; Watanabe et al., 1994; Bernstein et al., 1989 and Watson et al., 1993).

Various capsaicin compositions have been developed over the years, in particular, the psoriatic composition of U.S. Pat. No. 4,486,450, the nasal composition of U.S. Pat. No. 5,134, 166, and the composition of U.S. Pat. No. 4,997,853, the anti-inflammatory composition of U.S. Pat. No. 5,560,910, the composition of U.S. Pat. No. 5,962,532, the composition for animals of U.S. Pat. No. 5,916,565, the stomach treatments of U.S. Pat. No. 5,889,041, the composition of U.S. Pat. No. 5,827,886, the patch with medication of U.S. Pat. No. 5,741,510, all of which are incorporated by reference herein.

U.S. Pat. No. 6,593,370 discloses a topical capsaicin preparation for the treatment of painful cutaneous disorders and neural dysfunction. The preparation contains a nonionic, amphoteric or cationic surfactant in an amount effective to eliminate or substantially ameliorate burning pain caused by capsaicin.

U.S. Pat. No. 6,573,302 discloses a cream comprising: a topical carrier wherein the topical carrier comprises a member selected from the group comprising lavender oil, myristal myristate, and other preservatives including, *hypericum perforatum arnica montana* capric acid; and 0.01 to 1.0 wt. % capsaicin; 2 to 10 wt. % an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

U.S. Pat. No. 6,348,501 discloses a lotion for treating the symptoms of arthritis using capsaicin and an analgesic, and a method for making.

U.S. Pat. No. 5,962,532 disclose methods and compositions for treating pain at a specific site with an effective concentration of capsaicin or analogues. The methods involve providing anesthesia to the site where the capsaicin or analogues thereof is to be administered, and then administering an effective concentration of capsaicin to the joint. The anesthesia can be provided directly to the site, or at remote site that causes anesthesia at the site where the capsaicin is to be administered. For example, epidural regional anesthesia can be provided to patients to which the capsaicin is to be administered at a site located from the waist down. By pretreating the site with the anesthetic, a significantly higher concentration of capsaicin can be used. Effective concentrations of capsaicin or analogues thereof range from between 0.01 and 10% by weight, preferably between 1 and 7.5% by weight, and more preferably, about 5% by weight. This provides for greater and more prolonged pain relief, for periods of time ranging from one week to several weeks. In some cases the pain relief may be more sustained because the disease that underlies the pain may improve due to a variety of factors including enhancement of physical therapy due to less pain in the soft tissues which may foster enhanced mobilization of soft tissues, tendons, and joints.

U.S. Pat. No. 5,910,512 disclose a water-based topical analgesic and method of application wherein the analgesic contains *capsicum, capsicum* oleoresin and/or capsaicin. This analgesic is applied to the skin to provide relief for rheumatoid arthritis, osteoarthritis, and the like.

U.S. Pat. No. 5,403,868 discloses novel capsaicin derivatives containing thio-urea, processes for the production thereof, pharmaceutical compositions containing them and use thereof as pharmaceuticals.

U.S. Pat. No. 5,178,879 discloses clear, water-washable, non-greasy gels useful for topical pain relief contain capsaicin, water, alcohol and a carboxypolymethylene emulsifier. A method of preparing the gels is also disclosed U.S. Pat. No. 5,021,450 relates to a new class of compounds having a variable spectrum of activities for capsaicin-like responses, compositions thereof, processes for preparing the same, and uses thereof. Compounds were prepared by combining phorbol related diterpenses and homovanillac acid analogs via esterification at the exocyclic hydroxy group of the diterpene. Examples of these compounds include 20-homovanillyl-mezerein and 20-homovanillyl-12-deoxyphorbol-13-phenylacetate.

U.S. Pat. No. 4,997,853 discloses a method and composition for treating superficial pain syndromes which incorporates capsaicin in a therapeutically effective amount into a pharmaceutically acceptable carrier and adding to this composition a local anesthetic such as lidocaine or benzocaine. The composition containing the anesthetic is then applied to the site of the pain. A variation on the treatment includes initial treatment with the composition containing the local anesthetic until the patient has become desensitized to the presence of capsaicin and subsequent treatment with a composition omitting the local anesthetic.

US application 20050019436 provides compositions and methods for relieving pain at a site in a human or animal in need thereof by administering at a discrete site in a human or animal in need thereof a dose of capsaicin in an amount effective to denervate a discrete site without eliciting an effect outside the discrete location, the dose of capsaicin ranging from 1 µg to 3000 µg.

US application 20040224037 claims a use of Capsaicin (8-methyl-n-vanillyl-6-nonenamide), its derivatives, vanilloids and *capsicum* extract, to combat and control HIV (humans immunodeficiency virus) and AIDS (acquired immunodeficiency syndrome). An evaluation of a *capsicum* sp consumption of a long term aids survivors group permitted a definition of more efficacious ways to administer the substance. capsaicin intravenous and by subcutaneous or intramuscular administration at low concentration implemented by using infuses, it inhibits HIV replication and stimulates the production and proliferation of lymphocytes and cells NK. Also it acts as desinfectant in macrophages, and has a power as anticancer and antioxidant agent. Moreover has the property to control and annihilate common opportunistic illnesses related to HIV due to its triple antibiotic characteristics.

US application 20040146590 provides methods and kits for the selective ablation of pain-sensing neurons. The methods comprise administration of a vanilloid receptor agonist to a ganglion in an amount that causes death of vanilloid receptor-bearing neurons. Accordingly, the present invention provides methods of controlling pain and inflammatory disorders that involve activation of vanilloid receptor-bearing neurons.

US application 20030133995 discloses a chemical composition for an ingestible capsaicin neutralizer to neutralize the effect of capsaicin on the oral cavity, tongue, and esophagus when capsaicin from hot peppers is ingested by a user comprised of an effective neutralizing amount of casein protein, or the salt thereof, an alkali earth metal halide, and the balance water.

US application 20030082249 discloses a composition for use in treating or preventing mucositis, and/or xerostomia, including capsaicin or capsaicin derivative, and one or more additional compounds useful in treating mucositis and/or xerostomia, wherein the composition is provided in an oral delivery vehicle. The term capsaicin derivative and capsaicinoid as used in the disclosure are interchangeable and generally refer to capsaicin analogs. Among the capsaicinoids useful in the practice of the disclosure are capsaicin, the N-phenylmethylalkenamide capsaicin derivatives; dihydrocapsaicin; norhydrocapsaicin; nordihydrocapsaicin; homocapsaicin; homohydrocapsaicin; homodihydrocapsaicin; civamide (cis-capsaicin); nonivamide; NE-19550 (N-[4-hydroxy-3-methoxyphenyl)methyl]-9Z-octadecanamide) (olvanil); NE-21610 (N-[(4-(2aminoethoxy)-3-methoxyphenyl)methyl]-9Z-octadecanamide) Sandoz Pharmaceutical Corp, East Hanover, N.J.); NE-28345 (N-(9Z-octadecenyl)-3-methoxy-4-hydroxyphenylacetamide; also known as N-oleyl-homovanillamide); and their analogs and derivatives (U.S. Pat. No. 5,762,963, which is incorporated herein by reference). NE-19550, NE-21610, and NE-28345 are discussed in Dray et al. (1990).

US application 20020058048 discloses a topical capsaicin preparation for the treatment of painful cutaneous disorders and neural dysfunction is disclosed. The preparation contains a nonionic, amphoteric or cationic surfactant in an amount effective to eliminate or substantially ameliorate burning pain caused by capsaicin.

US application 20010002406 discloses transdermal application of capsaicin (or a capsaicin analog) in a concentration from greater than about 5% to about 10% by weight to be an extremely effective therapy for treating neuropathic pain, so long as an anesthetic, preferably by means of a transdermal patch, is administered initially to the affected area to minimize the expected side effects from subsequent capsaicin application. Analogs of capsaicin with physiological properties similar to capsaicin are known (Ton 1955). For example, resiniferatoxin is described as a capsaicin analog by Blumberg, U.S. Pat. No. 5,290,816. U.S. Pat. No. 4,812,446, describes capsaicin analogs and methods for their preparation.

U.S. Pat. Nos. 4,493,848 and 4,564,633 disclose the derivatives of capsaicin, including short chain ester derivatives (C1-C6) of capsaicin for analgesia in human.

Figure 3:
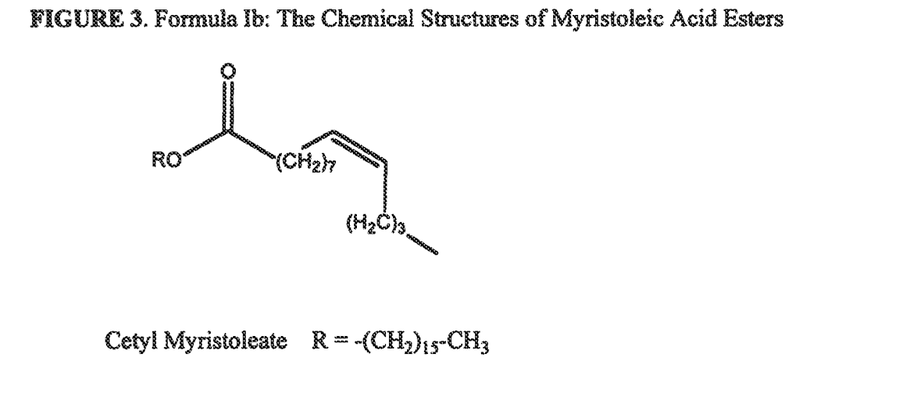
FIG. 3. Is a picture of the formula of the chemical structures of myristoleic acid esters.

Cetyl myristoleate (CMO) is the common name for cis-9-cetyl myristoleate and the structure of cetyl myristoleate is shown in FIG. 3. In 1972 Diehl (1994) discovered that Swiss albino mice did not get arthritis after injection of Freund's adjuvant. Eventually, he was able to determine that cetyl myristoleate was the factor present naturally in mice which was responsible for this protection. When cetyl myristoleate was injected into various strains of rats, it offered the same protection against arthritis. Cetyl myristoleate is a natural medium chain fatty acid found in certain animals, including cows, whales, beavers, and mice. It has been proposed that cetyl myristoleate acts as a joint "lubricant" and anti-inflammatory agent.

The rational for the use of cetyl myristoleate is that it may inhibit the production of inflammatory prostaglandins and leukotrienes. The process of inflammation involves the release of proinflammatory cytokines (e.g., interleukin 1β and tumor necrosis factor-α). Fatty acids, especially n-6 fatty acids, have been proposed to reduce chronic inflammation in patients with rheumatoid arthritis by reducing leukotriene B4 from stimulated neutrophils and of interleukin-1 monocytes (Kremer 2000; 1996). In addition, other suggested mechanisms for the anti-inflammatory response observed with fatty acid treatment are reduced expression and activity of proteoglycan degrading enzymes and cytokines, suppression of leukocyte function, changes in adhesion molecule expression and apoptosis triggering, and alterations in signal transduction and membrane fluidity (Kremer 2000; Curtis 2000 and Heraud 2000).

U.S. Pat. Nos. 5,569,676, 4,113,881 and 4,049,824 disclose the use of cetyl myristoleate in both osteoarthritis and rheumatoid arthritis and several scientific studies have documented the benefit of cetyl myristoleate in relieving pain based upon the animal studies and several case histories (Siemendi 1997; Cochran 1996; Elkins 1997 and Hesslink 2002). In a double-blind study, 106 individuals with various types of arthritis who had failed to respond to non-steroidal anti-inflammatory drugs received cetyl myristoleate (540 mg per day orally for 30 days), while 226 others received a placebo. These individuals also applied cetyl myristoleate or placebo topically, according to their perceived need. Some 63.5% of those receiving cetyl myristoleate improved, compared with only 143% of those receiving the placebo (Siemandi 1997 and Cochran 1996).

A need exists for a topical preparation which eliminates or substantially ameliorates initial stinging pain caused by capsaicin observed in the administration with anti-inflammatory properties thereby making the preparation tolerable in long-term administration.

The purpose of the present application is to disclose the unexpected discovery that esters of capsaicin have significantly less burning pain at the site of the application and the synergistic combination of the esters of capsaicin and esters of myristoleic acid are extremely effective in treating pain in humans. The present invention does not rely on topical anesthetics, such as lidocaine (Entry 5310, p. 786 Merck Index, Tenth Edition 1983) and benzocaine (ethyl aminobenzoate, Entry 3710, p. 546 Merck Index, Tenth Edition, 1983) into formulations containing capsaicin, and then applying such formulations for the initial period of treatment to eliminate the painful burning from the application of capsaicin, allowing the patient to continue therapy while being able to feel through the skin onto which the cream is applied.

SUMMARY OF THE INVENTION

The present invention provides for certain novel pharmaceutical compositions containing synergistic combination of ester derivatives of capsaicin and ester derivatives of myristoleic acid that are highly lipophilic. The compounds of capsaicin and myristoleic acid set forth herein are enzymatically cleaved to the parent compound. Thus, the compounds set forth herein provide for a novel form of therapy of diseases amendable to treatment with capsaicin and myristoleic acid.

The synergistic combination of the ester derivatives of capsaicin and the ester of myristoleic acid of the present invention would have significant utility over capsaicin and existing derivatives currently described in the patent and scientific literature. In particular, in view of their high lipophilicity, non-irritation to the skin, significantly less burning sensation at the site of application and stability, these new derivatives would be more bioavailable when administered topically compared to capsaicin. In addition, because of their stability and non-toxic nature, these agents can be made more readily available to the general public. The inventors have surprisingly and unexpectedly discovered that the ester derivatives of capsaicin in combination with the esters of myristoleic acid have therapeutic utility in treating pain in humans. These compounds thus provide for a novel form of therapy of any disease or condition wherein capsaicin and myristoleic acid are believed to be of benefit, including but not limited to, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

The present invention generally pertains to pharmaceutical compositions containing a compound of formula (Ia):

wherein CAP refers to collectively the capsaicins represented in FIG. 1 and a compound of formula (Ib):

wherein MCO refers to myristoleic acid represented in FIG. 3.

In formulae Ia and Ib, R is selected from alkyl groups of up to about 18 carbon atoms and aryl groups of up to about 18 carbon atoms and alkylene group of up to about 18 carbon atoms and an arylene group of up to about 18 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula Ia and Ib include methyl, ethyl, propyl, butyl, hexyl, heptyl, octyl, dodecyl, 1-pentadecyl, 1-heptadecyl, 1-hexadecyl, 1-octadecyl and the like groups.

Examples of suitable branched chain alkyl groups in formula Ia and Ib include isopropyl, sec-butyl, t-butyl, 2-methylbutyl, 2-pentyl, 3-pentyl and the like groups.

Examples of suitable cyclic alkyl groups in formula Ia and Ib include cyclopropyl, cyclobutyl, cyclopentyl and cyclohexyl groups.

Examples of suitable "alkenyl" groups in formula Ia and Ib include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula Ia and Ib are pyridinyl, thienyl or imidazolyl.

As noted herein, the expression "halo" is meant in the conventional sense to include F, Cl, Br, and I.

Among the compounds represented by the general Formula Ia and Ib, preferred compounds are such in which R is one of the following groups: methyl, ethyl, propyl, butyl, pentyl, hexyl, 1-pentadecyl, 1-heptadecyl, 1-hexadecyl, 1-octadecyl, isobutyl, methoxyethyl, ethoxyethyl, benzyl and nicotinyl.

The compounds of Formula Ia are esters of capsaicin and its analogues and compounds of Ib are esters of myristoleic acid. However, information in the literature does not disclose or indicate the esters of capsaicin have any utility as pro-drug forms in combination with the esters of myristoleic acid suitable for oral and topical delivery for treating diseases such as post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

The present invention also generally pertains to pharmaceutical compositions comprising one or more of the compounds set forth above.

Accordingly, one aspect of the present invention is to disclose the combination of esters of capsaicin and esters of myristoleic acid in the treatment of post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

In particular, the esters of capsaicin and esters of myristoleic acid described herein may be used for the preparation of therapeutic compositions in the treatment of post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor in humans.

Preferably, the compositions useful in the method may be topically applied to the human in need of such therapy.

The method of the present invention neither destroys healthy, uninfected tissue nor results in any local or systemic side effects, scarring, disfigurement or discomfort to the human treated. Furthermore, the use of the esters of the present invention reduces the occurrence of skin irritation and rashes unlike the free capsaicin. The method includes the use of ester of capsaicin and ester of myristoleic acid for the administration to an area of the human which is anticipated to evidence, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

In accordance with the method according to this invention, regular use of the esters of capsaicin and esters of myristoleic acid is meant to mean application of the esters of capsaicin and esters of myristoleic acid at least once a day to the body surface containing post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

There is further disclosed a method for the treatment of post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor, comprising the application of a cream or douche containing either an ester of capsaicin or mixtures thereof and either an ester of myristoleic acid or mixtures thereof, to the affected area of the human body.

There is also disclosed a method for treating post-herpetic neuralgia, shingles (herpes zoster), diabetic neuropathy, post-mastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor, said method comprising the application of either an ester of capsaicin or mixtures thereof and either an ester of myristoleic acid or mixtures thereof, to the affected area of a human for a period of time and at a sufficient concentration to eradicate symptoms in the human.

The pharmaceutical compositions of the present invention can additionally include one or more pharmaceutically acceptable excipients. One of ordinary skill in the art would be familiar with pharmaceutically acceptable excipients. For example, the pharmaceutically acceptable excipient may be a water soluble sugar, such as mannitol, sorbitol, fructose, glucose, lactose, and sucrose.

The pharmaceutical compositions of the present invention may further comprise one or more pharmaceutically acceptable antioxidants. Any pharmaceutically acceptable antioxidant known to those of ordinary skill in the art is contemplated for inclusion in the present pharmaceutical compositions. For example, the pharmaceutically acceptable antioxidant may be selected from the group consisting of ascorbic acid, sodium ascorbate, sodium bisulfate, sodium metabisulfate and monothio glycerol.

The pharmaceutical compositions of the present invention may further comprise one or more pharmaceutically acceptable preservatives. Any pharmaceutically acceptable preservative known to those of ordinary skill in the art is contemplated for inclusion in the present pharmaceutical compositions. Examples of such preservatives include methylparaben, methylparaben sodium, propylparaben, propylparaben sodium, benzalkonium chloride, and benzthonium chloride.

The pharmaceutical compositions of the present invention may further comprise one or more pharmaceutically acceptable buffering agents. Any pharmaceutically acceptable buffering agent known to those of ordinary skill in the art is contemplated for inclusion in the present pharmaceutical compositions. Examples of such buffering agents include of monobasic sodium phosphate, dibasic sodium phosphate, sodium benzoate, potassium benzoate, sodium citrate, sodium acetate, and sodium tartrate.

The pharmaceutical compositions of the present invention can include any concentration of a compound of the present invention. For example, the concentration of compound may be 0.1 mg/ml to 1000 mg/ml or greater. In certain particular embodiments, the concentration of compound is 1 mg/ml to 500 mg/ml. In still further embodiments, the concentration of compound is 5 mg/ml to 100 mg/ml.

In some embodiments of the present invention, the pharmaceutical composition includes more than one of the novel compounds set forth above. In other embodiments of the present invention, the pharmaceutical composition includes one or more secondary therapeutic agents directed to a disease or health-related condition, as discussed below.

The present invention also generally pertains to methods of treating or preventing a pathological condition in a subject, comprising providing a therapeutically effective amount of any of the pharmaceutical compositions set forth above, and administering the composition to the subject. The subject can be any subject, such as a mammal or avian species. In certain particular embodiments, the mammal is a human. The human may be an individual affected by or at risk of developing a disease or condition amenable to therapy with capsaicin. For example, the pathological condition may be post-herpetic neuralgia, shingles (herpes zoster), diabetic neuropathy, post-mastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

The pharmaceutical composition of the present invention may be administered to the subject by any method known to those of ordinary skill in the art. For example, the method of administering the composition to the subject may include oral, topical, nasal, inhalational, rectal, or vaginal. Methods of administration are discussed in greater detail in the specification below.

In certain embodiments of the methods of the present invention, the method involves administering to the subject a therapeutically effective amount of a secondary agent. The secondary agent can be any pharmacologic agent known or suspected to be of benefit in the treatment or prevention of a disease or health-related condition in a subject. For example, in some embodiments, the secondary agent is a secondary pain relieving agent. Secondary pain relieving agents, which include morphine, are well-known to those of ordinary skill in the art. Examples of such agents include aspirin, acetaminophen (Tylenol) or other aspirin-like drugs called nonsteroidal anti-inflammatory drugs (NSAIDs), weak narcotics such as codeine (Tylenol with codeine), hydrocodone (Vicodin or Lortab), Percocet, Percodan or propoxyphene (Darvon), strong opioids such as morphine, Demerol, Dilaudid, fentanyl (duragesic patches) and methadone.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention is based on the inventors' discovery of certain pharmaceutical compositions containing esters of myristoleic acid and derivatives of capsaicin that are highly lipophilic, nonirritating, and thus allow higher concentrations for improved bioavailability following administration in a cream or ointment formulations. The pharmaceutical compositions of the present invention include esters of capsaicin and esters of myristoleic acid. These compounds are suitable by any route of administration, but are particularly suited for oral or topical administration in view of their lipid solubility. These pharmaceutical compositions thus provide for a novel form of therapy of any disease or condition wherein capsaicin or myristoleic acid is believed to be of benefit, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

DETAILED DESCRIPTION OF THE INVENTION

A. Capsaicin Derivatives of the Present Invention

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification, the singular forms "a," "an" and "the" include plural referents unless the context clearly dictates otherwise. Thus, for example, reference to "a pharmacologically active agent" includes a combination of two or more pharmacologically active agents, and the like. In describing the present invention, the following terminology will be used in accordance with the definitions set out below.

As used herein in the claim(s), when used in conjunction with the word "comprising", the words "a" or "an" may mean one or more than one. As used herein "another" may mean at least a second or more.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The term "topical administration" is used in its conventional sense to mean delivery of a topical drug or pharmacologically active agent to the skin or mucosa.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

The term "capsaicin or capsaicins" as used herein is intended to encompass not only the compound capsaicin, but also homocapsaicin, nordihydrocapsaicin, dihydrocapsaicin, homodihydrocapsaicin or any compounded mixture thereof (see FIG. 1).

The present invention provides for certain novel pharmaceutical compositions containing ester derivatives of capsaicin and ester derivatives of myristoleic acid that are highly lipophilic. The ester of capsaicin and the ester of myristoleic acid set forth herein are enzymatically cleaved to the parent compound. Thus, the pharmaceutical compositions set forth herein provide for a novel form of therapy of diseases amendable to treatment with capsaicin and esters of myristoleic acid.

The combination of the ester derivatives of capsaicin and the ester of myristoleic acid of the present invention would have significant utility over capsaicin or myristoleic acid and existing derivatives currently described in the patent and scientific literature. In particular, in view of their high lipophilicity, non-irritation to the skin, significantly less burning sensation at the site of application and stability, these derivatives would be more bioavailable when administered topically compared to capsaicin or myristoleic acid. In addition, because of their stability and non-toxic nature, these agents can be made more readily available to the general public.

The inventors have surprisingly and unexpectedly discovered that the ester derivatives of capsaicin in combination with the esters of myristoleic acid have therapeutic utility in treating pain in humans. These compositions thus provide for a novel form of therapy of any disease or condition wherein capsaicin or myristoleic acid is believed to be of benefit, including but not limited to, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

The present invention generally pertains to pharmaceutical compositions containing a compound of formula (Ia):

R—CO-CAP     (Ia)

wherein CAP refers to collectively the capsaicins represented in FIG. 1 and a compound of formula (Ib):

MCO-O—R     (Ib)

Wherein MCO refers to myristoleic acid represented in FIG. 3.

In formula Ia and Ib, R is selected from alkyl groups of up to about 18 carbon atoms and aryl groups of up to about 18 carbon atoms and alkylene group of up to about 18 carbon atoms and an arylene group of up to about 18 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula Ia and Ib include methyl, ethyl, propyl, butyl, hexyl, heptyl, octyl, dodecyl, 1-pentadecyl, 1-heptadecyl 1-hexadecyl, 1-octadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula Ia and Ib include cyclopropyl, cyclobutyl, cyclopentyl and cyclohexyl groups.

Examples of suitable "alkenyl" groups in Ia and Ib include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula Ia and Ib are pyridinyl, thienyl or imidazolyl.

As noted herein, the expression "halo" is meant in the conventional sense to include F, Cl, Br, and I.

Among the compounds represented by the general Formula Ia and Ib, preferred compounds are such in which R is one of the following groups: methyl, ethyl, propyl, butyl, pentyl, hexyl, 1-pentadecyl, 1-heptadecyl, 1-hexadecyl, 1-octadecyl, isobutyl, methoxyethyl, ethoxyethyl, benzyl and nicotinyl.

The compounds of Formula Ia are esters of capsacin and its analogues and compounds of Ib are esters of myristoleic acid. However, information in the literature do not disclose or indicate the esters of capsaicin have any utility as prodrug forms in combination with the esters of myristoleic acid suitable for oral and topical delivery for treating diseases such as post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

B. Methods of Synthesis

The compounds used in the present invention can be prepared by any method known to those of ordinary skill in the art. For example, the esters of myristoleic acid can be obtained commercially as oil, powder or wax (EHP Products Inc, USA). Various methods have been described in the literature pertaining to the synthesis of a number of esters of carboxylic acids and phenols (March's Advanced Organic Chemistry: Reactions, Mechanisms, and Structure, 5th Edition, by Michael B. Smith and Jerry March, John Wiley and Sons, Inc, 2001).

One method that has been utilized for efficient preparation of the ester of capsaicin of the present invention is through dissolution of the compound in methylene dichloride. Since capsaicin USP27 conatins >95% of capsaicins, to this solution slightly in excess of 1.1 mole equivalent of anhydrous triethylamine is added with stirring at room temperature. To this solution slightly in excess of 1 mole equivalent of an acid chloride is added with stirring while keeping the temperature around 25° C. After that, the solution was refluxed for 2-5 hours and stirred for 12-17 hours at room temperature. The reaction mixture was then washed with equal amount of water three to four times to remove the unreacted amine and its salt in a separating funnel. The organic phase was washed 3-4 times with dilute hydrochloric acid solution in a separating funnel to remove any amine present in the organic solution. The reaction mixture was then washed with equal amount of 10% sodium carbonate solution three to four times to remove the unreacted acid and salts in a separating funnel. The reaction mixture was then washed with equal amount of water three to four times in a separating funnel. The organic phase was dried with anhydrous sodium sulfate overnight and the methylene dichloride was removed in a rotary evaporator under vacuum. The resultant oily or waxy material is called the ester capsaicin as all of the phenols present capsaicin is converted into the corresponding ester.

C. Pharmaceutical Compositions

Certain embodiments of the present invention pertain to pharmaceutical compositions comprising the esters of capsaicins and esters of myristoleic acid set forth herein.

The phrases "pharmaceutical," "pharmaceutically," or "pharmacologically acceptable" refer to molecular entities and compositions that do not produce an unacceptably adverse, allergic or other untoward reaction when administered to an animal, or human, as appropriate. As used herein, "pharmaceutical" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients to treat the disease of interest, such as other anti-cancer agents or anti-inflammatory agents, can also be incorporated into the compositions.

Pharmaceutical compositions of the present invention will include an effective amount of one or more of the ester derivatives of capsaicin and the ester derivatives of myristoleic acid set forth herein that are clinically determined to be useful in the treatment of the particular disease under consideration. One of ordinary skill in the art would be familiar with what type of dosage is required for treatment of the particular pathological condition that is present in the subject. No undue experimentation would be involved. When used for therapy, the compositions of the present invention are administered to subjects in therapeutically effective amounts. For example, an effective amount of the ester of capsaicin in a patient with diabetic neuropathy may be an amount that promotes the healing of the pain associated with the neuropathy. The dose will depend on the nature of the disease, the subject, the subject's history, and other factors. Preparation of such compositions is discussed in other parts of this specification.

As discussed above, the derivatives of capsaicin set forth herein have greater lipophilicity and significantly less irritation to the skin than capsaicin. One advantage of these esters is that they can be incorporated into a cream or ointment form at a higher percentage by weight as compared to capsaicin. Another advantage is that these compositions have a very low toxicity and irritation to the skin as compared to formulations of capsaicin.

The compositions of the capsaicin derivatives and myristoleic acid derivatives of the present invention can be delivered by any method known to those of ordinary skill in the art. For example, the pharmaceutical compositions can be delivered by topical or oral delivery routes.

Compositions employing the esters of capsaicin and esters of myristoleic acid set forth herein will contain a biologically effective amount of the derivative. As used herein a biologically effective amount of a compound or composition refers to an amount effective to alter, modulate or reduce disease conditions. One of ordinary skill in the art would be familiar with methods of determining a biologically effective amount of a therapeutic agent. For example, a biologically effective amount may be about 0.1 mg/kg to about 50 mg/kg or greater The therapeutic combination of esters of capsaicin and esters of myristoleic acid of the present invention may be administered alone or in combination with one or more additional therapeutic esters of the present invention. In other embodiments, the therapeutic combination of ester of capsaicin and ester of myristoleic acid is administered in combination with one or more secondary forms of therapy directed to the disease or condition to be treated. These are discussed in greater detail below. Additional pharmaceutical compounds may be administered in the same pharmaceutical composition, or in a separate dosage form, such as in a separate oral, intramuscular, or intravenous dosage forms taken at the same time.

The therapeutic agents of the present invention may be supplied in any form known to those of ordinary skill in the art. For example, the therapeutic agent may be supplied as a liquid or as a solution. The pharmaceutical compositions may contain a preservative to prevent the growth of microorganisms. It must be chemically and physically stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like.

The formulations according to the invention having been described herein may influence the ordinarily skilled artesian to make similar formulations using components that will be known in the art, without departing from the invention which is claimed herein.

The pharmaceutical formulations of the esters of capsaicin and esters of myristoleic acid according to the present invention offer several advantages over the existing formulations. They can be topically applied and relatively high concentrations of the esters of capsaicin can be loaded into patients with high bioavailability. Thus the frequency of dosage can be reduced. Thus within the spirit, the invention is related to improved formulations and methods of using the same when administering such formulations to patients. As mentioned herein above a number of excipients may be appropriate for use in the formulation which comprises the composition according to the present invention. The inclusion of excipients and the optimization of their concentration for their characteristics such as for example ease of handling or carrier agents will be understood by those ordinarily skilled in the art not to depart from the spirit of the invention as described herein and claimed herein below.

Following preparation of the pharmaceutical compositions of the present invention, it may be desirable to quantify the amount of the esters of capsaicin and esters of myristoleic acid in the pharmaceutical composition. Methods of measuring concentration of a drug in a composition include numerous techniques that are well-known to those of skill in the art. Selected examples include chromatographic techniques. There are many kinds of chromatography which may be used in the present invention: drug-specific assays, adsorption, partition, ion-exchange and molecular sieve, and many specialized techniques for using them including column, paper, thin-layer chromatography, gas chromatography, and high performance liquid chromatography (HPLC). One of ordinary skill in the art would be familiar with these and other related techniques.

D. Moisturizing Agents

Certain topical formulations of the present invention may contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, *aloe barbadensis, aloe-barbadensis* extract, *aloe barbadensis* gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

E. Antioxidants

Certain topical formulations of the present invention may also contain one or more antioxidants. Non-limiting examples of antioxidants that can be used with the compositions of the present invention include acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

F. Pathological Conditions to be Treated or Prevented

As noted in other parts of this specification, there is substantial evidence that capsaicin would be beneficial in the treatment of a wide variety of pathological conditions. The term "treat" or "treatment" means that the symptoms associated with one or more conditions mentioned above are alleviated or reduced in severity or frequency and the term "prevent" means that subsequent occurrences of such symptoms are avoided or that the frequency between such occurrences is prolonged.

Conditions amenable to treatment or prevention with capsaicin are specifically detailed for post-herpetic neuralgia (Bernstein et al., 1989; Watson et al., 1993), diabetic neuropathy (Capsaicin Study Group, 1992), postmastectomy pain syndrome (Watson and Evans 1992; Dini et al., 1993), oral neuropathic pain, trigeminal neuralgia, and temperomandibular joint disorders (Epstein and Marcoe, 1994; Hersh et al., 1994), cluster headache (following intranasal application; Marks et al., 1993), osteoarthritis (McCarthy and McCarthy, 1992), and dermatological and cutaneous conditions (Hautkappe et al., 1998).

Examples of pathological conditions responsive to capsaicin therapy include, but are not limited to, post-herpetic neuralgia, shingles (herpes zoster), diabetic neuropathy, postmastectomy pain syndrome, oral neuropathic pain, trigeminal neuralgia, temperomandibular joint disorders, pruritus, cluster headache, osteoarthritis, arthritis pain, rhinopathy, oral mucositis, cutaneous allergy, detrusor hyperreflexia, loin pain/hematuria syndrome, neck pain, amputation stump pain, reflex sympathetic dystrophy and pain due to skin tumor.

Examples of pathological conditions responsive to esters of myristoleic acid include, but are not limited to, arthritis pain, osteoarthritis and inflammation.

It is expected that the novel pharmaceutical composition containing ester derivatives of capsaicin and ester derivatives of myristoleic acid set forth herein would be beneficial in the treatment and prevention of any of the diseases set forth above. One of ordinary skill in the art would be familiar with the many diseases and conditions that would be amenable to treatment with one or more of the ester derivatives of capsaicin set forth herein.

G. Secondary Therapies

Some embodiments of the claimed methods of the present invention involve administering to the subject a secondary form of therapy in addition to one or more of the therapeutic combination of ester derivatives of capsaicin and ester derivatives of myristoleic acid set forth herein. For example, if the disease is a hyperproliferative disease, such as cancer, the secondary therapy may be a chemotherapeutic agent, radiation therapy, surgical therapy, immunotherapy, gene therapy, or other form of anticancer therapy well-known to those of ordinary skill in the art. If the disease is an inflammatory disease such as arthritis, exemplary secondary forms of therapy include non-steroidal anti-inflammatory agents, steroids and immunosuppressant therapy.

In order to increase the effectiveness of the therapeutic agent disclosed herein, it may be desirable to combine the therapeutic agent of the present invention with the secondary therapeutic agent. These compositions would be provided in a combined amount effective to provide for a therapeutic response in a subject. One of ordinary skill in the art would be able to determine whether the subject demonstrated a therapeutic response. This process may involve administering the therapeutic agent of the present invention and the secondary therapeutic agent to the subject at the same time. This may be achieved by administering a single composition or pharmacological formulation that includes both agents, or by administering two distinct compositions or formulations, at the same time, wherein one composition includes the ester derivative of capsaicin and ester derivative of myristoleic acid of the present invention and the other includes the secondary agent.

Alternatively, the therapeutic agent of the present invention may precede or follow the treatment with the secondary agent by intervals ranging from minutes to weeks. In embodiments where the secondary agent and the ester derivatives of the present invention are separately administered, one would generally ensure that a significant period of time did not expire between the time of each delivery, such that the secondary agent and the therapeutic agent of the present invention would still be able to exert a beneficial effect on the subject. In such instances, it is contemplated that one may administer both modalities within about 24-48 h of each other and, more preferably, within about 12-24 h of each other, and even more preferably within about 30 minute-6 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the therapeutic agent of the present invention is "A" and the secondary agent, such as chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the compositions of the present invention to a patient will follow general protocols for the administration of therapeutic agents, such as chemotherapy where the disease to be treated is cancer. It is expected that the treatment cycles would be repeated as necessary.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Butyryl Ester of Capsaicin USP27 (Formula I, $R=C_3H_7$)

A mixture of 30.5 gm (~0.1M) of capsaicin USP27 (HUBEI XIANGXI CHEMICAL INDUSTRY CO., LTD, China), 16.7 ml (0.12M) of anhydrous triethylamine (Spectrum Chemicals) and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was kept at room temperature and 12.8 ml (0.12M) of butyryl chloride was added from the funnel into the mixture slowly with stirring. After the addition, the mixture was refluxed for 3-6 hours and stirred for 10-45 hours at room temperature. The mixture was transferred into a separating funnel and washed successively with 2×500 ml of water, 2×500 ml of dilute hydrochloric acid, 2×500 ml of 10% sodium bicarbonate solution and 3×500 ml of type water. The organic layer was separated, dried with anhydrous magnesium sulfate and the dichloromethane was removed under vacuum to produce a clear, yellow viscous oil (95% of theoretical).

Example 2

Preparation of Hexanoyl Ester of Capsaicn USP27 (Formula I, $R=CH_3—(CH_2)_4$)

The compound was prepared essentially as described in Example 1, using n-hexanoyl chloride instead of butyryl chloride. The product was recovered as a low melting viscous yellow oil.

Example 3

Preparation of Palmitoyl Ester of Capsaicn USP27 (Formula I, $R=CH_3—(CH_2)_{14}$)

The compound was prepared essentially as described in Example 1, using n-palmitoyl chloride instead of butyryl chloride. The product was recovered as a waxy yellow solid.

Example 4

Preparation of a Topical Gel Containing Butyryl Ester of Capsaicin USP27 and Cetyl Myristoleate Three compositions of capsaicin butyrate, shown in Table 1, each with a batch size of 500 gm of the gel, were prepared according to the following procedure.

TABLE 1

The Composition of Topical Gel containing Capsaicin Butyrate

| COMPOSITIONS INGREDIENTS NAME | Amount I | Amount II | Amount III |
|---|---|---|---|
| In a suitable container, the following ingredients were added and mixed with a mixer to make a smooth paste. | | | |
| Purified water | 300 ml | same | same |
| Potassium Sorbate | 0.5 gm (0.1%) | same | same |
| Methyl Paraben Sodium | 0.5 gm (0.1%) | same | same |

TABLE 1-continued

The Composition of Topical Gel containing Capsaicin Butyrate

| COMPOSITIONS INGREDIENTS NAME | Amount I | Amount II | Amount III |
|---|---|---|---|
| Sodium Citrate | 1.5 gm (0.3%) | same | same |
| Disodium Edetate | 2.5 gm (0.5%) | same | same |
| Propyl Paraben Sodium | 0.05 gm (0.01%) | same | same |
| Carbopol Ultrez 10 | 15.0 gm (3.0%) | same | same |
| Xanthum gum | 1.5 gm (0.3%) | same | same |
| The following ingredients were mixed together in a separate container and the mixture was added to the above paste with vigorous stirring. | | | |
| Capsaicin butyrate | 1.25 gm (0.25%) | 2.50 gm (0.5%) | 5.0 gm (1.0%) |
| Cetyl Myristoleate (40%) | 50.0 gm (10%) | same | same |
| Tween 80 | 1.50 gm (0.3%) | same | same |
| Hallbrite BHB | 15.0 gm (3.0%) | same | same |
| Eugenyl Acetate | 5.00 gm (1.0%) | same | same |
| Cyclomethicone | 10.0 gm (2.0%) | same | same |
| Ascorbyl Palmitate | 1.50 gm (0.3%) | same | same |
| Lavender oil | 2 ml (0.4%) | same | same |
| The mixture was stirred thoroughly with a stirrer and the following ingredients were added under stirring. | | | |
| Triethanolamine | 8.0 gm (1.6%) | same | same |
| Purified water qs to make | 500 gm | 500 gm | 500 gm |

A shiny white gel was formed and the pH of the gel was between 6.4 and 6.6.

Example 5

Preparation of a Topical Gel Containing Palmitoyl Ester of Capsaicin USP27 and Cetyl Myristoleate Three compositions of capsaicin palmitate, shown in Table 2, each with a batch size of 500 gm of the gel, were prepared according to the following procedure.

TABLE 2

The Composition of Topical Gel containing Capsaicin Palmitate and Cetyl Myristoleate

| COMPOSITIONS INGREDIENTS NAME | Amount I | Amount II | Amount III |
|---|---|---|---|
| In a suitable container, the following ingredients were added and mixed with a mixer to make a smooth paste. | | | |
| Purified water | 300 ml | same | same |
| Potassium Sorbate | 0.5 gm (0.1%) | same | same |
| Methyl Paraben Sodium | 0.5 gm (0.1%) | same | same |
| Sodium Citrate | 1.5 gm (0.3%) | same | same |
| Disodium Edetate | 2.5 gm (0.5%) | same | same |
| Propyl Paraben Sodium | 0.05 gm (0.01%) | same | same |
| Carbopol Ultrez 10 | 15.0 gm (3.0%) | same | same |
| Xanthum gum | 1.5 gm (0.3%) | same | same |
| The following ingredients were mixed together in a separate container and the mixture was added to the above paste with vigorous stirring. | | | |
| Capsaicin Palmitate | 2.50 gm (0.5%) | 5.00 gm (1.0%) | 7.50 gm (1.5%) |
| Cetyl Myristoleate (40%) | 50.0 gm (10.0%) | same | same |
| Tween 80 | 1.50 gm (0.3%) | same | same |
| Hallbrite BHB | 15.0 gm (3.0%) | same | same |
| Eugenyl Acetate | 5.00 gm (1.0%) | same | same |
| Ascorbyl Palmitate | 1.50 gm (0.3%) | same | same |
| Cyclomethicone | 10.0 gm (2.0%) | | |

TABLE 2-continued

The Composition of Topical Gel containing Capsaicin Palmitate and Cetyl Myristoleate

| COMPOSITIONS INGREDIENTS NAME | Amount I | Amount II | Amount III |
|---|---|---|---|
| Lavender oil | 2.0 ml (0.4%) | same | same |
| The mixture was stirred thoroughly with a stirrer and the following ingredients were added under stirring. | | | |
| Triethanolamine | 8.0 gm (1.6%) | same | same |
| Purified water qs to make | 500 gm | 500 gm | 500 gm |

A shiny white gel was formed and the pH of the gel was between 6.4 and 6.6.

Example 6

Preparation of Capsules Containing Palmitoyl Capsaicin USP27 and Cetyl Myristoleate The capsule composition is compounded from the following ingredients given in Table 3.

TABLE 3

The composition for the preparation of capsules.

| Ingredient | Amount I | Amount II |
|---|---|---|
| Palmitoyl-Capsaicin USP27 | 5.40 parts | 10.8 parts |
| Microcrystalline Cellulose | 19.60 parts | 14.20 parts |
| Cetyl Myristoleate Powder (20% in corn starch) | 350.00 parts | 350.00 parts |
| Ascorbyl palmitate | 20.00 parts | 20.00 parts |
| Silicon dioxide | 2.50 parts | 2.50 parts |
| Sodium lauryl sulfate | 2.50 parts | 2.50 parts |
| Total | 400.00 parts | 400.00 parts |

PREPARATION I: The palmitoyl-capsaicin USP27 (Table 3; Amount I) is intensively milled with ten times its weight of Cetyl Myristoleate powder, the milled mixture is admixed with the remaining amount of the Cetyl Myristoleate powder, microcrystalline cellulose, ascorbyl palmitate sodium lauryl sulfate and silicon dioxide. The mixed powder is again milled and the composition is filled into 500 mg capsule in a conventional capsule loading machine. Each capsule contains 5.40 mg of palmitoyl-capsaicin USP27 (approximately 50,000 SHU equivalent in each capsule) and 70 mg of Cetyl Myristoleate and is an oral dosage unit composition with effective therapeutic action.

PREPARATION II: The palmitoyl-capsaicin-USP27 (Table 3; amount II) is intensively milled with five times its weight of Cetyl Myristoleate powder, the milled mixture is admixed with the remaining amount of the Cetyl Myristoleate powder, microcrystalline cellulose, ascorbyl palmitate, sodium lauryl sulfate and silicon dioxide. The mixed powder is again milled and the composition is filled into 500 mg capsule in a conventional capsule loading machine. Each capsule contains 10.8 mg of palmitoyl-capsaicin USP27 (approximately 100,000 SHU equivalent in each capsule) and 70 mg of Cetyl. Myristoleate and is an oral dosage unit composition with effective therapeutic action.

Example 7

Toxicity Assessment of the Inventive Composition

A 0.5% of butyryl-capsaicin USP27 and 4% Cetyl Myristoleate gel as described in example 4 was applied to the forearm of 10 healthy individuals twice daily for a two-week period in an outpatient clinic. No patients complained of burning, irritation, scaling or redness after the cream. Patients returned to the clinic after having used the gel for two weeks for a visual inspection of the forearm area. The examining physician noted no redness, irritation or scaling in the area where the solution had been applied.

Example 8

Treatment of Pain with the Topical Formulation of Butyryl Capsaicin USP27 and Cetyl Myristoleate Case I. Patient with Diabetic Neuropathy in the Feet A 53 year old hispanic male has developed Type 2 diabetes a year ago and has diabetic neuropathy in the feet. He was given the 0.5% butyryl-capsaicin USP27 and 4% Cetyl Myristoleate gel and the following is his testimony on the effectiveness of the oil for the treatment of cold sores. "I was diagnosed with type 2 diabetes last year. I also have neuropathy in my feet. I had an ulcer on my foot and was treated by a local pediatric doctor in San Antonio. My ulcer has since been cleared up. I control my diabetic ailment with a low-carb diet only, with no medication. I have also lost 40 lbs. since my diagnosis last year. I however feel pain on the bottom of my feet at times. Since taking the cream by application on my feet, I have noticed much less discomfort than usual. The comfort that I noticed has lasted up to 24 hrs per-application. This cream really helps my condition and would like to let your research company to know about your product".

Case II. Patient with Pain in Dislocated Finger

A 45 year old white male developed constant pain in the finger due to dislocation and has to be injected cortisone every 3 months to alleviate the pain. He was given 1% butyryl capsaicin USP27 and 4% Cetyl Myristoleate gel for topical application. He gave the following testimony about the treatment. "Every 3 months or so, I have a cortisone shot in a finger I dislocated a few years ago. I used the 1% gel given to me. It did a very good job for the pain and making movement a lot easier. The swelling was reduced as well as the pain. I did however, find that the product does have a tendency to get a little warm. That's a good thing, other than it still transfers after hand washing, and you might get a little warm where you don't need it. I feel like this product would be beneficial for people who can not or who would rather not take oral pain medication"

Case III. Patient with Severe Diabetic Neuropathy

A 40 year old white female developed diabetic neuropathy in 2000 and was given 0.5% butyryl capsaicin and 4% Cetyl Myristoleate gel for treating her pain in the feet. She gave the following testimony about the treatment. "I was diagnosed with neuropathy in 2000. There never has been much they could do for me other than give me pain medication that's addictive. At this time, I'm on Neurontin 1800 mg a day, Vicodin 5.6 tablets a day. Diclofenac 150 mg a day, and also get injections in my feet. In the last 7 months I have had 5 different cast on my left foot. Since my left foot has a cast my right foot has become worse because all of my weight has been on my right foot. I used the crème and within 30 min. I could feel the difference. Later I was up walking and realized there was no pain at all. At night I don't sleep well because of the pain, but I was able to go to sleep the whole night through without cramps and pain. My cast will be coming off in 8 days and I can't wait to try it on my left foot".

Case IV. Patient with Pinched Nerve Pain

A 65 year old white female developed pain due to pinched nerve and was treated with the 0.5% butyryl capsaicin USP27 and 4% Cetyl Myristoleate gel. She gave the following testimony about the treatment. "Over a period of years, periodically a pinched nerve would occur in the left lower side of my back. This required chiropractic treatment which at times was not always successful requiring several additional treatments. After using the cream, my pain has disappeared and that was three days ago and still no pain".

Case V. Patient with Severe Diabetic Neuropathy

A 49 year old white male developed diabetic neuropathy in 2001 and was given 0.5% butyryl capsaicin USP27 and 4% Cetyl Myristoleate gel for treating his pain in the feet. He gave the following testimony about the treatment. "I have diabetic neuropathy brought on by extreme intra-venous application of antibiotics for a six day period. Since that time I have experienced unmanageable pain causing sleep depravation, anxiety with no relief on the market. Prescriptions for anti-depressants were given by my personal physician but to no avail Now with this cream I can sleep without any disturbances. Nothing on the market today could help me without the use of addicting narcotics that were marginally effective at best".

Case VI. Patient with Severe Neuropathy

A 62 year old white female developed neuropathy in 1975 and was given 0.5% butyryl capsaicin USP27 and 4% Cetyl Myristoleate gel for treating her pain in the feet. She gave the following testimony about the treatment. "My neuropathy numbness in feet and hands first started after back surgery in 1975 my L4 and 5 were fused and some disks removed. The numbness and pain increased after surgery for a double mastectomy which was botched by a doctor inexperienced at this surgery in 1988 causing sever pain in my abdominal muscles and up my chest. In 1992 I was in the hospital for depression a new doctor prescribed Percocet medication for my pain. The Percocet helped but I had to take 8 a day 5/325 mgs with anti depression medication at the time. The pain was so overwhelming after 4 years that I decided one day to end it all and I was found by my husband on the floor. I had kept my pain a secret over the 4 years hoping it would just eventually go away and I had never told my family that I was suffering so much. I had overdosed with the Percocet in an attempt to end my pain for good. I recovered some and I tried to cut back on the Percocet and got down to 1 a day to prevent addiction. The increase in pain and numbness was causing me to stumble when I walked. A neurologist in 1998 suggested that I try Neurontin which is used for epilepsy. I think I was taking 100 mgs 3 times a day at first then increased in 6 weeks to 200 mgs 3 times a day, when that failed we went up to 300 mgs 3 times a day. The 300 mgs was starting to help some but they had to increase to 800 mgs 5 times a day to really help my pain. This helped more than the Percocet alone but I still needed to keep the Percocet at reduced amounts. I fell and broke my back fusion in 2000. New back surgery attempted to fuse my back again but in 2003 doctors had to use rods and pins to secure it. With each surgery my numbness and pain would increase. I tried water therapy and various physical therapies but nothing could relieve my pain. I have had other injuries as well, in 2002 a broken right ankle and compression fracture in my right knee and in 2003 I broke my left ankle. In October 2005 a doctor specializing in neurological disorders said the Neurontin was probably weakening my bones and switched me to a generic version of the same medication and dropped the dose to 50 mgs a day. My pain increased immediately and I went through withdrawals with the smaller dose. This doctor said if the pain didn't decrease I was to increase one tablet more a day each week till the end of the 4th week and return to him. I never went back to this doctor and just increased back to 800 mgs 5 times a day to cope with the pain, burning, and itching feelings. I had to take depression medication again at this time. I tried a new topical cream just this week Jul. 11, 2006 being developed in San Antonio, Tex. One of my most disruptive symptoms in my feet would cause me to involuntarily jump in bed and I was beginning to feel this come on when I applied the cream to my left foot. The symptoms just stopped! Usually this symptom would last several hours to even days. I have burning sensations in both hands and up my forearm but after applying this cream I had my first relief from that burning feeling since my back surgeries in 2003! This cream has done more to relieve my symptoms than both Percocet and Neurontin has ever done for me! I now have renewed hope to stop taking all this internal medication that is bound to hurt my liver and is weakening my bones".

We claim:

1. A method of treating pain in a subject in need thereof, comprising administering to the subject a pharmaceutical composition comprising:

(a) a compound of formula (Ia):

wherein $R_1$ is selected from the group consisting of
$(CH_2)_4(CH)_2CH(CH_3)_2$ (capsaicin ester);
$(CH_2)_5(CH)_2CH(CH_3)_2$ (homocapsaicin ester);
$(CH_2)_5CH(CH_3)_2$ (nordihydrocapsaicin ester);
$(CH_2)_6CH(CH_3)_2$ (dihydrocapsaicin ester);
$(CH_2)_7CH(CH_3)_2$ (homodihydrocapsaicin ester);
$(CH_2)_6CH_3$ (n-vanillyloctanamide ester);
$(CH_2)_7CH_3$ (nonivamide ester);
$(CH_2)_8CH_3$ (n-vanillyldecanamide ester); and
$(CH_2)_4(CH)_2CH(CH_3)_2$ (civamide ester); and (b) an ester of myristoleic acid of formula (Ib):

wherein R of formula (Ia) and (Ib) are independently selected from alkyl groups of up to 18 carbon atoms and aryl groups of up to 18 carbon atoms and alkylene group of up to 18 carbon atoms and an arylene group of up to 18 carbon atoms, wherein the alkyl, aryl and alkylene groups may be substituted or unsubstituted, branched or straight chains, wherein R may contain heteroatoms selected from the group consisting of O, N, Cl, F, Br, I and S and may be straight chained or branched.

2. The method of claim 1, wherein the pharmaceutical composition is an oral or topical formulation.

3. The method of claim 2, wherein the topical formulation is a cream, lotion, spray, wipe, or drop formulation.

4. The method of claim 2, wherein the pharmaceutical composition comprises one or more additional pharmaceutical agents.

5. The method of claim 4, wherein the one or more additional pharmaceutical agents is selected from the group consisting of fungicidal or fungistatic agents, bacteriocidal or bacteriostatic agents, viricidal or viristatic agents, cytotoxic agents, non-steroidal anti-inflammatory agents, NMDA antagonists, COX inhibitors, steroidal anti-inflammatory agents, opiate pain relieving agents, tramadol, and μ-opiate receptor agonists and antagonists.

6. The method of claim 2, wherein the composition further comprises one or more pharmaceutically acceptable excipients.

7. The method of claim 6, wherein the excipients include one or more pharmaceutically acceptable antioxidants.

8. The method of claim 7, wherein the antioxidant is ascorbic acid, sodium ascorbate, sodium bisulfite, sodium metabisulfate, curcumin, curcumin derivatives, ursolic acid, resveratrol, resveratrol derivatives, alpha-lipoic acid or monothioglycerol.

9. The method of claim 6, wherein the excipients include one or more pharmaceutically acceptable preservatives and/or buffering agents.

10. The method of claim 9, wherein the buffering agent is monobasic and dibasic sodium phosphate, sodium benzoate, potassium benzoate, sodium citrate, sodium acetate or sodium tartrate.

11. The method of claim 9, wherein the preservative is methylparaben, methylparaben sodium, propylparaben, propylparaben sodium, benzalkonium chloride or benzthonium chloride.

12. The method of claim 2, wherein the pharmaceutical composition comprises one or more pharmaceutically acceptable polysaccharides.

13. The method of claim 12, wherein the polysaccharide is selected from the group consisting of dextran sulfate, pectin, modified pectin, insoluble 1,3-β-D glucan, micronized 1,3-β-D glucan, soluble 1,3-β-D glucan, phosphorylated 1,3-β-D glucan, aminated 1,3-β-D glucan and carboxymethylated 1,3-β-D glucan, sulfated 1,3-β-D glucan, insoluble 1,3/1,6-β-D glucan, micronized 1,3/1,6-β-D glucan, soluble 1,3/1,6-β-D glucan, phosphorylated 1,3/1,6-β-D glucan, aminated 1,3/1,6-β-D glucan and carboxymethylated 1,3/1,6-β-D glucan or sulfated 1,3/1,6-β-D glucan.

14. The method of claim 2, wherein the pharmaceutical composition comprises an amount selected from the group consisting of from 0.025% to 20% by weight of the ester(s) of capsaicin; from 0.05% to 20% by weight of the ester(s) of capsaicin; and from 0.05% to 10% by weight of the ester(s) of capsaicin.

15. The method of claim 2, wherein the pharmaceutical composition comprises an amount selected from the group consisting of from 0.025% to 99% by weight of the ester(s) of myristoleic acid; from 1% to 99% by weight of the ester(s) of myristoleic acid; and from 4% to 99% by weight of the ester(s) of myristoleic acid.

16. The method of claim 2, wherein the composition is administered orally, nasally, topically, rectally or vaginally.

17. The method of claim 1, wherein the pain is caused by a disease selected from the group consisting of post-herpetic neuralgia, shingles (herpes zoster), diabetic neuropathy, trigeminal neuralgia, temperomandibular joint disorders, pruritus, cluster headache, osteoarthritis, rhinopathy, oral mucositis, cutaneous allergy, detrusor hyperreflexia and reflex sympathetic dystrophy.

18. The method of claim 1, wherein the pain is selected from the group consisting of postmastectomy pain syndrome, oral neuropathic pain, arthritis pain, loin pain/hematuria syndrome, neck pain, amputation stump pain and pain due to skin tumor.

19. The method of claim 1, wherein the compound of part (a) is capsaicin palmitate.

20. The method of claim 19, wherein the myristoleic acid ester of part (b) is cetyl myristoleate.

21. The method of claim 20, wherein the composition is formulated for topical administration.

22. The method of claim 21, wherein the composition comprises a pharmaceutically acceptable excipient selected from the group consisting of Hallbrite BHB, carbopol ultrez10, eugenyl acetate, eugenyl acetate, TWEEN 80, xanthum gum, lavender oil, triethanolamine, disodium edentate, methyl paraben sodium, propyl paraben sodium, potassium sorbate and combinations thereof.

* * * * *